United States Patent [19]

Goto et al.

[11] Patent Number: 5,023,244
[45] Date of Patent: Jun. 11, 1991

[54] ANTI-DEMENTIA AGENTS

[75] Inventors: Masayoshi Goto, Tokyo; Nobutaka Demura; Tsutomu Osaki, both of Saitama, all of Japan

[73] Assignee: Hoechst Japan Limited, Tokyo, Japan

[21] Appl. No.: 407,696

[22] Filed: Sep. 15, 1989

Related U.S. Application Data

[63] Continuation of Ser. No. 42,866, Apr. 14, 1987, abandoned.

[30] Foreign Application Priority Data

Apr. 25, 1986 [JP] Japan .................................. 61-94738

[51] Int. Cl.$^5$ ............................................ A61K 31/70
[52] U.S. Cl. ........................................ 514/46; 514/45; 536/24; 536/26
[58] Field of Search ..................... 536/24, 26; 514/45, 514/46

[56] References Cited

U.S. PATENT DOCUMENTS

| | | | |
|---|---|---|---|
| 3,864,483 | 2/1975 | Stein et al. | 536/24 |
| 3,992,531 | 11/1976 | Prasad et al. | 536/24 |
| 4,029,884 | 6/1977 | Stein et al. | 536/24 |
| 4,167,565 | 9/1979 | Stein et al. | 536/24 |
| 4,224,438 | 9/1980 | Fauland | 536/24 |

FOREIGN PATENT DOCUMENTS

| | | | |
|---|---|---|---|
| 2632951 | 2/1977 | Fed. Rep. of Germany | 536/24 |
| 2610985 | 9/1977 | Fed. Rep. of Germany | 536/24 |
| 2730846 | 1/1978 | Fed. Rep. of Germany | 536/24 |

OTHER PUBLICATIONS

Reddington, M., Adenosine: Recept. Modulation Cell Function, Proc. Intl. Workshop Adenosine Xanthime Deriv; 1985, pp. 181–189, Oxford, England.
Phillis et al. (I), Can. J. Physiol. Pharmacol. V. 57 (11), 1289–1312 (1979).
Phillis et al., (II), Life Sci., 17(7), 1085–1094 (1975).
Bazil et al., J. Neurochem., 47(2), 547–553, (1986).
Anand Srivastava, et al.; J. Neurochem., 35 (4), pp. 905–914 (1980).
Okada et al., (II) Euro. J. Pharm., vol. 61, pp. 137–146 (1980).
Okada et al. (II), Neurobiol. Chem. Transm., Proc. Taniguchi Symposium Brain Sci., First, Publ. 1979, pp. 223–234, Wiley, New York.
Benzodiazepine Blockage of Passive-Avoidance Task in Mice: A State-Dependent Phenomenon, J. B. Patel et al., Psychopharmacology, 61, pp. 25–28 (1979).
The Comparative Effects of Benzodiazepines, Progabide and PK 9084 on Acquisition of Passive Avoidance in Mice, C. L. Broekkamp et al., Psychopharmacology (1984) 83:122–125.

*Primary Examiner*—Johnnie R. Brown
*Assistant Examiner*—L. Eric Crane
*Attorney, Agent, or Firm*—Finnegan, Henderson, Farabow, Garrett and Dunner

[57] ABSTRACT

An anti-dementia agent comprising as an active ingredient an adenosine derivative is disclosed. The anti-dementia agent is useful in the therapy of various types of dementia, especially senile dementia. Examples of the adenosine derivative include L-$N^6$-phenylisopropyladenosine, 2-chloroadenosine, $N^6$-cyclohexyladenosine, adenosine-5'-(N-cyclopropyl)carboxamide.

6 Claims, No Drawings

ANTI-DEMENTIA AGENTS

This application is a continuation of application Ser. No. 042,866 filed Apr. 14, 1987, now abandoned.

(1) FIELD OF THE INVENTION

The present invention relates to anti-dementia agents. More particularly, it is concerned with anti-dementia agents containing an adenosine derivative as an active ingredient.

The anti-dementia agents of the invention are useful in the therapy of various types of dementia, especially of senile dementia.

(2) DESCRIPTION OF PRIOR ARTS

Diseases concurrent with deficits of memory such as senile dementia have become a serious medical and social problem as the average span of life has been longer in recent years. Heretofore, however, almost none of drugs are useful in the therapy of such diseases, and urgent development of the useful drugs is desired.

It is an object of the invention to provide therapeutic agents for cerebral dysfunctions, particularly for dementia to meet the above requirement. Cerebral dysfunctions as referred to in the invention represent those which are caused primarily by disorders of the central nervous system including glia cells and those which are caused primarily by disorders of the cerebro-vascular system. Dementia as referred to in the invention means diseases manifesting symptoms as indicated below.

Dementia is divided into two etiological types. One of them is Alzheimer-type dementia which is a disease associated with degeneration of cerebral nerve cells by uncertain causes. The Alzheimer-type dementia is a progressive disease at the initial stage of which rapidly aggravating failure of memory, loss of orientation for time and place and decline of willingness are observed. As the disease progresses, the serious symptoms such as the disturbance of speech and poor expression appear. The other is cerebro-vascular dementia caused by cerebrovascular disorders.

As described above, dementia patients suffer from such symptoms as loss of mental faculties, deficits of memory, disturbances of thinking in the abstracts, aphasia, poriomania and agnosia. These disorders are based on the impairment of acquisition, retention and recall of the memory.

As a result of extensive studies for development of therapeutic agents useful for patients suffering from deficits of memory associated with dementia, we have found that some adenosine derivatives are very useful for deficits of memory. Since there are no drugs up to now that are useful for dementia, it is expected that the adenosine derivatives are valuable for the therapy of symptoms associated with dementia, particularly, of deficits of memory.

The present invention comprises anti-dementia agents containing as the active ingredient an adenosine derivative having the formula (I)

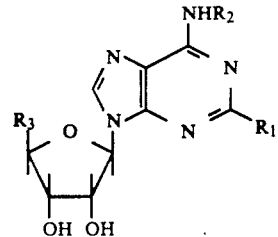

wherein $R_1$ represents a hydrogen atom or a halogen atom, $R_2$ represents a hydrogen atom, an alkyl group, a cycloalkyl group or an aralkyl group and $R_3$ represents a hydroxymethyl group or the group $-CONHR_4$ in which $R_4$ represents a hydrogen atom, an alkyl group, a cycloalkyl group or an aralkyl group with the exception that $R_1$ and $R_2$ are both hydrogen atoms and $R_3$ is a hydroxymethyl group.

As examples of the halogen atom as a substituent in the above formula (I) are mentioned chlorine, bromine and iodine. Particularly preferred is chlorine. As examples of the preferred alkyl group are mentioned alkyl groups containing from 1 to 4 carbon atoms such as methyl, ethyl, n-propyl, isopropyl, n-butyl, isobutyl and tert-butyl. As examples of the preferred cycloalkyl group are mentioned cycloalkyl groups containing from 3 to 7 carbon atoms such as cyclopropyl, cyclobutyl, cyclopentyl, cyclohexyl and cycloheptyl. As examples of the preferred aralkyl groups are mentioned phenylalkyl groups containing in the alkyl moiety from 1 to 4 carbon atoms such as benzyl, phenethyl, phenylpropyl, phenylisopropyl and phenylbutyl.

As preferred adenosine derivatives in the present invention are mentioned compounds having the formula (II)

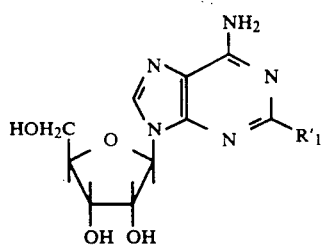

wherein $R'_1$ represents a halogen atom, compounds having the formula (III)

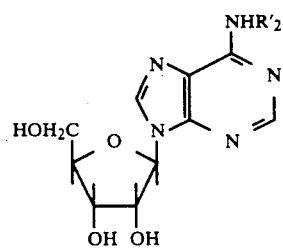

wherein $R'_2$ represents an alkyl group, a cycloalkyl group or an aralkyl group and compounds having the formula (IV)

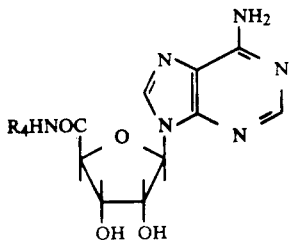

(IV)

wherein R4 has the same meaning as defined above.

As examples of the adenosine derivative according to the invention are mentioned:
2-chloroadenosine,
2-bromoadenosine,
$N^6$-methyladenosine,
$N^6$-ethyladenosine,
$N^6$-cyclopropyladenosine,
$N^6$-cyclohexyladenosine,
$N^6$-benzyladenosine,
$N^6$-phenethyladenosine,
$N^6$-phenylpropyladenosine,
$N^6$-phenylisopropyladenosine,
adenosine-5'-(N-methyl)carboxamide,
adenosine-5'-(N-ethyl)carboxamide,
adenosine-5'-(N-propyl)carboxamide,
adenosine-5'-(N-cyclopropyl)carboxamide,
2-chloro-$N^6$-methyladenosine,
2-chloro-$N^6$-cyclohexyladenosine,
2-chloro-$N^6$-phenylisopropyladenosine,
$N^6$-cyclohexyladenosine-5'-(N-ethyl)carboxamide, and
2-chloro-$N^6$-cyclohexyladenosine-5'-(N-ethyl)carboxamide.

The adenosine derivatives (I) are known compounds in the sense that they are disclosed per se in literatures For example, the compounds (II) are described in Proc. Natl. Acad. Sci. USA, 77, 5547-5551 (1981), and the compounds (III) and (IV) in Life Sci., 28, 2083-2097 (1981). Whereas these compounds are pharmacologically adenosine agonists which are active at adenosine receptors, their anti-dementia activities are not known.

Kobiler et al. reported in Pharmacol. Biochem. and Behav., 2, 9-17 (1974) that adenosine, a compound of the formula (I) in which $R_1$ and $R_2$ are hydrogen atoms respectively and $R_3$ is a hydroxymethyl group, inhibits long-term formation of deficits of memory caused by an inhibitor of RNA synthesis, 2,6-diaminopurine. The activity, however, is not high sufficiently to allow for clinical use in the therapy.

As a result of extensive studies, we have found that the above-mentioned adenosine derivatives (I) are very highly active for improving deficits of memory. Their activities are much superior as compared with adenosine itself.

As compared with pharmacologically active doses, the adenosine derivatives (I) are so low in toxicity that they may be given consecutively. For example, acute toxicity (LD$_{50}$) in mice by intraperitoneal administration is shown in Table 1.

TABLE 1

| Acute toxicity (LD$_{50}$ mg/kg) | |
|---|---|
| 2-Chloroadenosine | 45 |
| L-$N^6$-Phenylisopropyladenosine | 31 |

Results of experiments will be described below in details to indicate that the adenosine derivatives (I) are active in the therapy of deficits of memory for patients with dementia.

EXPERIMENT 1

In general, memory is composed of the following three processes: Initially memory is acquired by learning and then retained, followed by recall as needed.

In order to investigate effects of the adenosine derivatives (I) on memory, an experiment was performed in ICR male mice according to the passive avoidance task. The passive avoidance task and the induction of amnesia by cycloheximide are experimental methods usually employed (Naoki Yamazaki et al.: Jap. J. Psychopharmacol., 3, 127 (1983)). The detailed method is described below. The apparatus used for the experiment was a plastic box 24 cm in height, 20 cm in width and 23 cm in length with a floor of iron grids at the corner of which was placed a platform 8 cm in length, 8 cm in width and 1.5 cm in height. When a mouse placed in the box was subjected to electric stimulus with a current of 0.3 mA for a period of approximately 3 seconds, the mouse escaped onto the platform. After subsequent non-stimulus period of 8 seconds, the mouse was subjected to the electric stimulus for an additional period of approximately 5 seconds. By this method, the mouse acquired memory of aversion that the electric stimulus would be delivered whenever the animal got off the platform, thus the passive avoidance task was established. The learning was judged to be established if the mouse placed on the platform under non-stimulus condition immediately after the training remained on it for 30 seconds or longer.

The test to observe whether or not a mouse retained memory of aversion was performed 24 hours after the training and percent memory retention was calculated according to the following equation:

$$\text{Percent memory retention (\%)} = \frac{\text{Number of the animals remaining on the platform for 3 min. or longer}}{\text{Number of the animals tested}} \times 100$$

In order to induce deficits of memory, the animal was intraperitoneally administered 15 min prior to the training with a physiological saline solution of cycloheximide at a dose of 120 mg/kg., and then subjected to the electric stimulus for training.

Improving effect of the adenosine derivatives on the retrieval process of the memory impaired by cycloheximide was examined. A memory retention test was performed 24 hours after training. An intraperitoneal administration was done 75 min. prior to the test respectively for L-$N^6$-phenylisopropyladenosine (Compound A) and $N^6$-cyclohexyladenosine (Compound C), 60 min. prior to the test respectively for 2-chloroadenosine (Compound B) and adenosine-5'-(N-cyclopropyl)carboxamide (Compound E) and 45 min. prior to the test for adenosine-5'-(N-ethyl)carboxamide (Compound D). Results of the experiment are shown in Table 2. Marked improvement was observed with each of the adenosine derivatives. The results demonstrate that these adenosine derivatives improve the impaired retrieval process of memory.

TABLE 2

| Experimental group | Doses of the adenosine derivative (I) (μg/kg) | Number of animals | Percent memory retention (%) |
| --- | --- | --- | --- |
| Control (Physiol. saline + Physiol. saline) | — | 76 | 60.5 |
| Cycloheximide + physiol. saline | — | 80 | 22.5+ |
| Cycloheximide + Compound A | 50 | 19 | 36.8 |
|  | 100 | 20 | 55.0* |
| Cycloheximide + Compound B | 500 | 20 | 35.0 |
|  | 1000 | 21 | 52.4* |
| Cycloheximide + Compound C | 10 | 27 | 14.8 |
|  | 100 | 24 | 20.8 |
|  | 300 | 27 | 66.7* |
| Cycloheximide + Compound D | 3 | 28 | 39.3 |
|  | 7 | 26 | 42.3 |
|  | 10 | 35 | 51.4* |
| Cycloheximide + Compound E | 1 | 28 | 25.0 |
|  | 3 | 20 | 40.0 |
|  | 10 | 29 | 62.1* |
|  | 30 | 9 | 66.7* |

Note
+Significantly different from the control group at P < 0.01 (chi-square test)
*Significantly different from the group (Cycloheximide + physiol. saline) at P < 0.01 (chi-square test)

As a result of further studies on the effect of the adenosine derivatives (I) of the invention to improve memory, it was experimentally demonstrated that the effects were reduced by prior administration of theophylline which is a typical adenosine antagonist thereby suggesting that the memory-improving effects of the adenosine derivatives (I) were related with adenosine receptors.

Clinically, daily dose in adults is in the range between 2 mg and 1000 mg of the adenosine derivative, which depends upon the route of administration. Preferably, the dose is 10 mg-100 mg for L-$N^6$-phenylisopropyladenosine, 100 mg-1,000 mg for 2-chloroadenosine, 30 mg-400 mg for $N^6$-cyclohexyladenosine, and 2 mg-60 mg respectively for adenosine-5'-(N-ethyl)carboxamide and adenosine-5'-(N-cyclopropyl)-5-carboxamide.

The administration can be made intravenously, intramuscularly, orally or rectally. The intravenous administration can be by infusion as well as by instillation.

Pharmaceutical preparations containing the adenosine derivative (I) are prepared by a conventional method employing conventional recipients and additives The injectable preparations can be, for example, in the form of a powdery formulation for injection. The preparations can be prepared by dissolving in water a mixture with one or more of appropriate water-soluble recipients such as, for example, mannitol, sucrose, lactose, maltose, glucose and fructose, dividing the solution into vials or ampules and subjecting them to freeze drying and sealing.

Pharmaceutical preparations for oral administration can be ordinary tablets, capsules, granules, fine granules and powders as well as enteric preparations.

In preparing the enteric preparations, additives including recipients such as mannitol, sucrose, lactose, maltose, starch, silica and calcium phosphate, glidants such as talc and magnesium stearate, binders such as carboxymethylcellulose, methylcellulose, gelatin and gum arabic and disintegrating agents such as calcium carboxymethylcellulose are added as needed to form a preparation such as tablets, granules or fine granules, which is then coated with one or more of enteric bases such as cellulose acetate phthalate, hydroxypropylmethylcellulose phthalate, hydroxypropylmethylcellulose acetylsuccinate, polyvinyl alcohol phthalate, styrene-maleic anhydride copolymers, styrene-maleic acid copolymers, methyl methacrylate-methacrylic acid copolymers and methyl acrylate-methacrylic acid copolymers with coloring agents such as titanium oxides added as needed to prepare a final preparation. Alternatively, the enteric granules or fine granules thus prepared can be filled in capsules.

Enteric capsules can also be prepared by coating the capsules prepared by a conventional method with an enteric base as mentioned above or by employing capsules prepared with an enteric base alone or in admixture with gelatin.

Suppositories can be prepared by homogenously blending a mixture with a warm solution of a lipophilic base such as a semisynthetic base of cacao fat or a triglyceride of fatty acids in admixture with a monoglyceride of fatty acids and/or a diglyceride of fatty acids in various proportions or a hydrophilic base such as polyethylene glycol or glycerin and then placing the belnd in molds.

Examples of the invention will be given below.

EXAMPLE 1

To 1 g of 2-chloroadenosine and 16 g of sodium chloride was added injectable distilled with to a total volume of 2,000 ml. The solution was filtered sterile using a 0.22-micron millipore filter and divided into 5-ml ampules in a volume of 5 ml, which were melt sealed and sterilized in an autoclave to produce an injectable preparation.

EXAMPLE 2

Tablets were prepared by a conventional method from a mixture of 25 g of 2-chloroadenosine with 250 g of lactose, 150 g of corn starch, 150 g of calcium carboxymethylcellulose, 42 g of talc, 5 g of magnesium stearate and 3 g of silica. The tablets were coated with a dispersion of 40 g of hydroxypropylmethylcellulose, 2 g of macrogor 6000, 3.5 g of titanium oxides and 3 g of talc in 500 g of water to produce tablets each containing 5.7 mg of 2-chloroadenosine.

What is claimed is:

1. A method for the treatment of memory deficits, which comprises administering to an animal host an effective amount of a compound having the formula (I)

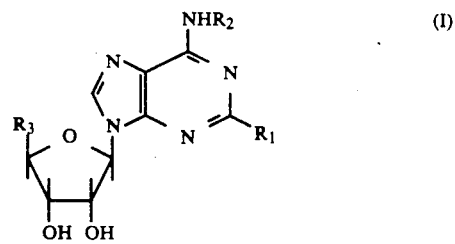

wherein $R_1$ represents a hydrogen atom or a halogen atom, $R_2$ represents a hydrogen atom, a $C_1$-$C_4$-alkyl group, a $C_3$-$C_7$-cycloalkyl group or a phenyl-$C_1$-$C_4$-alkyl group and $R_3$ represents a hydroxymethyl group or the group -$CONHR_4$ in which $R_4$ represents a hydrogen atom, a $C_1$-$C_4$-alkyl group, a $C_3$-$C_7$-cycloalkyl group or a phenyl-$C_1$-$C_4$-alkyl group, with the exception that $R_1$ and $R_2$ are both hydrogen atoms and $R_3$ is a hydroxymethyl group.

2. A method for the treatment of memory deficits according to claim 1, which comprises administering to an animal host an effective amount of a compound having the formula (I) in which $R_1$ represents a halogen atom, $R_2$ represents a hydrogen atom and $R_3$ represents a hydroxymethyl group.

3. A method for the treatment of memory deficits according to claim 2, which comprises administering to an animal host an effective amount of a compound having the formula (I) wherein $R_1$ represents a chlorine atom.

4. A method for the treatment of memory deficits according to claim 1, which comprises administering to an animal host an effective amount of a compound having the formula (I) in which $R_1$ represents a hydrogen atom, $R_2$ represents a $C_1$-$C_4$-alkyl group, a $C_3$-$C_7$-cycloalkyl group or a phenyl-$C_1$-$C_4$-alkyl group and $R_3$ represents a hydroxymethyl group.

5. A method for the treatment of memory deficits according to claim 4, which comprises administering to an animal host an effective amount of a compound having the formula (I) wherein $R_2$ is a $C_3$-$C_7$-cycloalkyl group or a phenyl-$C_1$-$C_4$-alkyl group.

6. A method for the treatment of memory deficits according to claim 1, which comprises administering to an animal host an effective amount of a compound having the formula (I) in which $R_1$ and $R_2$ respectively represent a hydrogen atom and $R_3$ represents the group -CONHR$_4$ wherein $R_4$ represents a hydrogen atom, a $C_1$-$C_4$-alkyl group, a $C_3$-$C_7$-cycloalkyl group or a phenyl-$C_1$-$C_4$-alkyl group.

* * * * *